US010082457B2

(12) United States Patent
Green et al.

(10) Patent No.: US 10,082,457 B2
(45) Date of Patent: Sep. 25, 2018

(54) ENSURING STABLE, PRECISE, AND ACCURATE OPTICAL ABSORPTION SPECTROSCOPIC TRACE GAS CONCENTRATION MEASUREMENTS IN THE PRESENCE OF TIME-VARYING ETALONS

(71) Applicant: International Business Machines Corporation, Armonk, NY (US)

(72) Inventors: William M. Green, Irvington, NY (US); Lionel Tombez, Neuchatel (CH); Eric Zhang, Princeton, NJ (US)

(73) Assignee: International Business Machines Corporation, Armonk, NY (US)

( * ) Notice: Subject to any disclaimer, the term of this patent is extended or adjusted under 35 U.S.C. 154(b) by 228 days.

(21) Appl. No.: 14/945,691

(22) Filed: Nov. 19, 2015

(65) Prior Publication Data

US 2017/0146448 A1    May 25, 2017

(51) Int. Cl.
*G01N 21/27* (2006.01)
*G01N 33/00* (2006.01)
G01N 21/17 (2006.01)
G01N 21/3504 (2014.01)
G01N 21/39 (2006.01)

(52) U.S. Cl.
CPC .......... *G01N 21/27* (2013.01); *G01N 21/274* (2013.01); *G01N 33/0047* (2013.01); *G01N 21/3504* (2013.01); *G01N 21/39* (2013.01); *G01N 2021/1748* (2013.01); *G01N 2201/13* (2013.01)

(58) Field of Classification Search
CPC .............. G01N 21/27; G01N 33/0047; G01N 2021/1748; G01N 2201/13
See application file for complete search history.

(56) References Cited

U.S. PATENT DOCUMENTS 6,044,094 A * 3/2000 Govorkov ................ G02F 1/39
372/21
6,922,645 B2 7/2005 Haaland et al.
(Continued)

OTHER PUBLICATIONS

D.S. Sayres et al., "A new cavity based absorption Instrument for detection of water isotopologues in the upper troposphere and lower stratosphere," Review of Scientific Instruments, vol. 80, Apr. 2009, 044102, 14 pages.

(Continued)

*Primary Examiner* — John Breene
*Assistant Examiner* — Mohammad Islam
(74) *Attorney, Agent, or Firm* — Vazken Alexanian; Michael J. Chang, LLC (57) ABSTRACT

Provided herein are techniques for improved optical absorption measurements in the presence of time-varying etalons. In one aspect, a method for dynamic etalon fitting for adaptive background noise reduction in an optical sensor is provided. The method includes the steps of: obtaining a zero-gas spectrum measured using the optical sensor; obtaining an analyte gas spectrum of a target trace gas measured using the optical sensor; comparing the zero-gas spectrum and the analyte gas spectrum using fit parameters that compensate for drifting etalons in the optical sensor; and dynamically extracting the drifting etalons from the analyte gas spectrum to retrieve concentration of the target trace gas.

17 Claims, 5 Drawing Sheets

(56) References Cited

U.S. PATENT DOCUMENTS

| | | |
|---|---|---|
| 7,251,037 B2 | 7/2007 | Jones |
| 7,800,764 B2 | 9/2010 | Kluczynski |
| 8,619,364 B2 | 12/2013 | Kluczynski et al. |
| 8,693,004 B2 | 4/2014 | Chandler et al. |
| 8,970,842 B2 | 3/2015 | Sun et al. |
| 2006/0072634 A1* | 4/2006 | Daiber .................... H01S 5/06 372/20 |
| 2012/0287418 A1* | 11/2012 | Scherer ................. G01N 21/61 356/51 |
| 2012/0312530 A1* | 12/2012 | Pope .................... E21B 47/102 166/250.01 |
| 2013/0209666 A1* | 8/2013 | Kamada ................. C23C 14/12 427/8 |
| 2015/0300942 A1 | 10/2015 | Mangold et al. |

OTHER PUBLICATIONS

M. Naftaly et al., "A method for removing etalon oscillations from THz time-domain spectra," Optics Communications, vol. 280, Dec. 2007, pp. 291-295.

X. Zhou et al., "Adaptive analysis of optical fringe patterns using ensemble empirical mode decomposition algorithm," Optics Letters, vol. 34, No. 13, Jul. 2009, pp. 2033-2035.

P. Werle, "Accuracy and precision of laser spectrometers for trace gas sensing in the presence of optical fringes and atmospheric turbulence," Applied Physics B, vol. 102, 2011, pp. 313-329 (published Aug. 2010).

* cited by examiner

ENSURING STABLE, PRECISE, AND ACCURATE OPTICAL ABSORPTION SPECTROSCOPIC TRACE GAS CONCENTRATION MEASUREMENTS IN THE PRESENCE OF TIME-VARYING ETALONS

FIELD OF THE INVENTION

The present invention relates to optical absorption spectroscopy, and more particularly, to techniques for improved optical absorption measurements in the presence of time-varying etalons.

BACKGROUND OF THE INVENTION

Optical trace gas sensors measure the concentration of gas species by absorption spectrometry. Direct absorption spectroscopy through silicon waveguides and other photonic platforms with large refractive index contrast can, however, suffer from strong etalons due to partial reflection from intermediate scattering points on the waveguide, as well as absorbing features (particularly C—H stretch absorption in the near-infrared) from particulate contaminants adsorbed onto the waveguide surface. Unwanted spectral features arising from the aforementioned fringe and contamination result in peak-to-peak fractional amplitude variations of about $1\times10^{-2}$, resulting in poor detection limits at long integration times. For reference, typical free-space optical spectroscopic trace gas detection systems are capable of detecting peak-to-peak fractional amplitude variations on the order of about $1\times10^{-5}$.

Conventional etalon subtraction (difference between sample and zero-gas trace) is insufficient for precision trace-gas monitoring in high index contrast integrated photonic platforms, particularly given the thermal dependence of fringing which causes slow changes in fringe free-spectral range over time.

Given the deleterious impact of these strong etalons, improved data analysis techniques are needed to restore trace gas concentration accuracy and precision.

SUMMARY OF THE INVENTION

Provided herein are techniques for improved optical absorption measurements in the presence of time-varying etalons. In one aspect of the invention, a method for a dynamic etalon fitting routine (DEF-R) for adaptive background noise reduction in an optical sensor is provided. The method includes the steps of: obtaining a zero-gas spectrum measured using the optical sensor; obtaining an analyte gas spectrum of a target trace gas measured using the optical sensor; comparing the zero-gas spectrum and the analyte gas spectrum using fit parameters that compensate for drifting etalons in the optical sensor; and dynamically extracting the drifting etalons from the analyte gas spectrum to retrieve concentration of the target trace gas.

A more complete understanding of the present invention, as well as further features and advantages of the present invention, will be obtained by reference to the following detailed description and drawings.

BRIEF DESCRIPTION OF THE DRAWINGS

FIG. 3B is a diagram illustrating conventional etalon subtraction applied to the raw waveguide sensor data in FIG. 2A, in comparison to the same applied to data acquired using a conventional free-space reference sensor, according to an embodiment of the present invention;

FIG. 3C is a diagram illustrating analysis using DEF-R applied to the raw waveguide sensor data in FIG. 2A, in comparison to the same applied to the data acquired using a conventional free-space reference sensor, according to an embodiment of the present invention;

FIG. 3D is a diagram correlating the normalized optical transmission through a conventional free-space reference sensor and a silicon waveguide chip sensor, when different methods for etalon mitigation are employed, according to an embodiment of the present invention;

DETAILED DESCRIPTION OF PREFERRED EMBODIMENTS

As provided above, slow changes in fringe free-spectral range occur over time. Thus, a simple etalon subtraction utilizing the difference between a sample and zero-gas trace is insufficient for precision trace-gas monitoring in high index contrast integrated photonic platforms, since a zero-gas trace becomes unusable due to etalon drift. Advantageously, provided herein is a dynamic etalon fitting-routine (DEF-R) which extends the time which the zero-gas trace remains usable, by introducing fitting parameters to account for fringe variation over time. As used herein, the term "dynamic" refers to the method by which the zero gas trace is updated over time, using a best fit to the analyte traces, with the transformation coefficients being the updated numerical parameters. The term "adaptive" applies as well, as the method describes adaption of the zero gas trace to changing ambient conditions, e.g., either by a lookup table acquired during a sensor calibration, or by using the acquired analyte trace data.

Figure 1A:
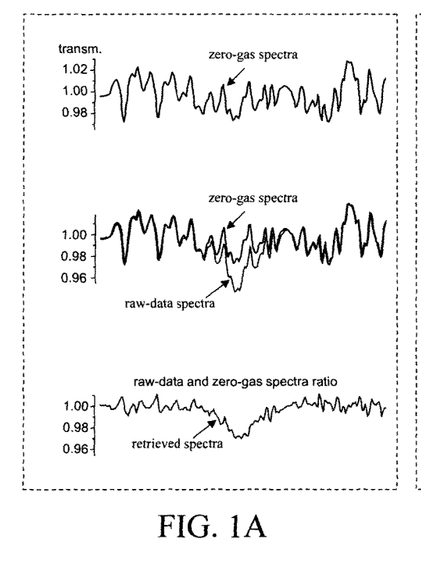
FIG. 1A is a diagram illustrating an example of conventional etalon subtraction.
Figure 1B:
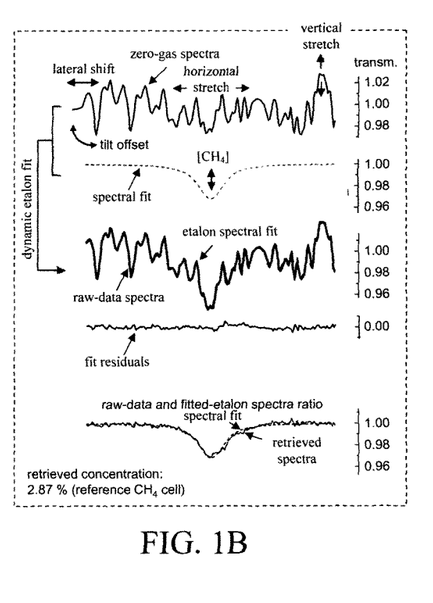
FIG. 1B is a diagram illustrating the effects of using free-parameters to perturb the zero-gas trace prior to subtraction/ratio calculations according to an embodiment of the present invention.

For example, a heuristic comparison between direct subtraction and the present DEF-R is shown in FIGS. 1A-B. Specifically, the transmission spectra in FIG. 1A illustrate an example of conventional etalon subtraction, and the transmission spectra in FIG. 1B illustrate, according to the present techniques, the effects of using free-parameters to perturb the zero-gas trace prior to the subtraction/ratio calculations. The analyte used in this particular example is methane ($CH_4$) gas. From the spectra retrieved using each scenario (shown as the lowest row in FIGS. 1A and 1B), it is clear that a signal-to-noise benefit is achieved in the case where fringes are imperfectly subtracted.

Conventional etalon subtraction involves a static zero-gas subtracted from an analyte data spectrum, which yields poor fringe-suppression ratio over time due to fringe drifts and contaminant adsorption/desorption. In contrast, the introduction of free-parameters into the zero-gas trace enables a method to account for these slow fringe variations over time. The generalized free-parameters are listed below:

Lateral shift—the small free-spectral range (FSR) shift due to thermal variations is observed (to first order) as a horizontal shift in the etalons. This is accounted for by utilizing a wider spectral span for the zero-gas to accommodate shifts up to 10% of the ramp range.

Horizontal stretch—accounts for the second order fringe variation due to change in the FSR from thermal fluctuations. Additionally, laser frequency ringing at the ramp onset causes a non-linear frequency (x-)axis, which artificially causes the fringe periodicity to vary in the time-domain.

Vertical stretch—possible variations in fringe/contaminant absorption amplitude.

Tilt offset—a sloped offset that accounts for any anomalies in power normalization.

Gas concentration—methane concentration is left as a free-parameter, which is a result of DEF-R analysis.

The above qualitative description of DEF-R demonstrates the generalized principle of the dynamic fitting algorithm; the introduction of multiple degrees of freedom on the zero-gas trace enables it to retain relevance over longer time periods where environmental factors may result in perturbations to the zero-gas spectra. Mathematically, the DEF-R algorithm is described by means of analytic transformations and interpolation on a known zero-gas trace $\varepsilon(t_{scan})$, resulting in a calculated dynamic spectra given as the product of analyte absorption spectra $\tau$ and transformed zero-gas trace $\Gamma[\varepsilon(t_{scan})]$:

$$\varphi(t_{scan}) = \tau(C_g, [t_{scan} \cdot \tilde{\upsilon} + \Delta\tilde{\upsilon}_{shift}]) \times \Gamma[\varepsilon(t_{scan})], \quad (1)$$

where $\tilde{\upsilon}$ and $\Delta\tilde{\upsilon}_{shift}$ are defined to indicate scan-time to wavenumber conversion and line-center shift respectively and $C_g$ defines the analyte concentration. It is to be noted that in the case of a practical measurement $t_{scan}$ can only be determined in discrete intervals, with intermediate time points requiring interpolation (a cubic spline is used for this purpose). The transformation of the zero-gas (etalon) spectra may be written as:

$$\Gamma[\varepsilon(t_{scan})] = \left[\overline{\varepsilon}\left(t_{scan} \cdot \frac{1}{\gamma_t} + \delta_t\right) - \langle\varepsilon(t_{scan})\rangle\right] \times \zeta + \quad (2)$$
$$\langle\varepsilon(t_{scan})\rangle + [(\lambda_{offset} \cdot t_{scan}) + \beta_{offset}].$$

In the above, $\overline{\varepsilon}$ is used to indicate the spline interpolation for spectral interpolation. $\gamma_t$ is the horizontal etalon stretch factor, and $\delta_t$ is the horizontal shift. $\zeta$ is the vertical stretch factor and the final bracketed term $(\lambda_{offset} \cdot t_{scan}) + \beta_{offset}$ involves a slope offset term to account for power fluctuations that results in baseline normalization inaccuracy. In the case of small concentration limits, where the etalon contribution dominates beyond any analyte concentration changes, $\tilde{\upsilon}$ and $\Delta\tilde{\upsilon}_{shift}$, are fixed by means of measurement of the analyte through a high-concentration reference cell. The remaining parameters $C_g$, $\gamma_t$, $\delta_t$, $\zeta$, $\lambda_{offset}$, and $\beta_{offset}$ are left as free parameters for least-mean-squares (LMS) fitting of $\varphi(t_{scan})$ to an experimentally acquired data spectra given by $D(t_{scan})$. This process, described by step 620 in FIG. 6 (see below), is denoted by LMS{$\varphi(t_{scan})$, $D(t_{scan})$} with resulting optimum fit parameters denoted by the set $\Omega^{opt.} = \{C_g^{opt}, \tilde{\upsilon}^{opt}, \Delta\tilde{\upsilon}_{shift}^{opt}, \gamma_t^{opt}, \delta_t^{opt}, \zeta^{opt}, \lambda_{offset}^{opt}, \beta_{offset}^{opt}\}$. The resulting spectral retrieval is given as:

$$\hat{\tau}_{ret.}(C_g^{opt}, [t_{scan} \cdot \tilde{\upsilon}^{opt} + \Delta\tilde{\upsilon}_{shift}^{opt}]) = \quad (3)$$
$$\frac{D(t_{scan})}{\left[\overline{\varepsilon}\left(t_{scan} \cdot \frac{1}{\gamma_t^{opt}} + \delta_t^{opt}\right) - \langle\varepsilon(t_{scan})\rangle\right] \times \zeta^{opt} +}$$
$$\langle\varepsilon(t_{scan})\rangle + [(\lambda_{offset}^{opt} \cdot t_{scan}) + \beta_{offset}^{opt}]$$

And the analyte concentration extraction $C_g^{opt}$ is the resulting parameter of interest for trace-gas monitoring.

Figure 2A:
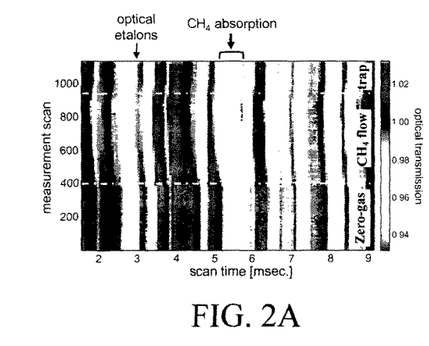
FIG. 2A is a diagram illustrating raw spectral compilation of 1100 sequential traces, captured during real-time methane gas ($CH_4$) flow.
Figure 2B:
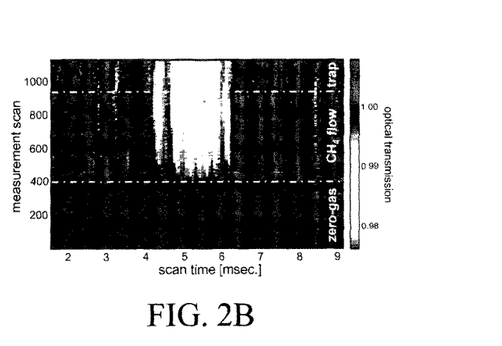
FIG. 2B is a diagram illustrating the same data as in FIG. 2A, but analyzed with DEF-R showing the visible enhancement of $CH_4$ spectral absorption according to an embodiment of the present invention.

Empirical Demonstration of Dynamic Etalon Fitting for Real-time $CH_4$ Variations: A raw acquired spectral ramp compilation is shown as a surface plot in FIG. 2A (i.e., raw data acquired as an example, without application of the present DEF-R method). The x-axis is scan time measured in milliseconds (msec) (having accounted for 100 hertz (Hz) ramp averaging) and the y-axis is measurement scan (approx 1.16 seconds (s) per measurement scan). The data in FIG. 2A is acquired with a silicon waveguide chip sensor and a free-space reference spectrometer enclosed within a sealed environmental chamber, into which a flow of dilute $CH_4$ in $N_2$ gas is injected, after which the chamber is sealed to trap the gas. The presence of $CH_4$ in the chamber is weakly visible at approximately scan 600. FIG. 2B shows the effect of DEF-R which enables suppression of fringing effects in the absorption spectrum, visibly enhancing the onset of $CH_4$ in the flow chamber. Note the difference in scale (as compared to FIG. 2A), which demonstrates the efficacy of fringe noise suppression using the DEF-R.

Figure 3A:
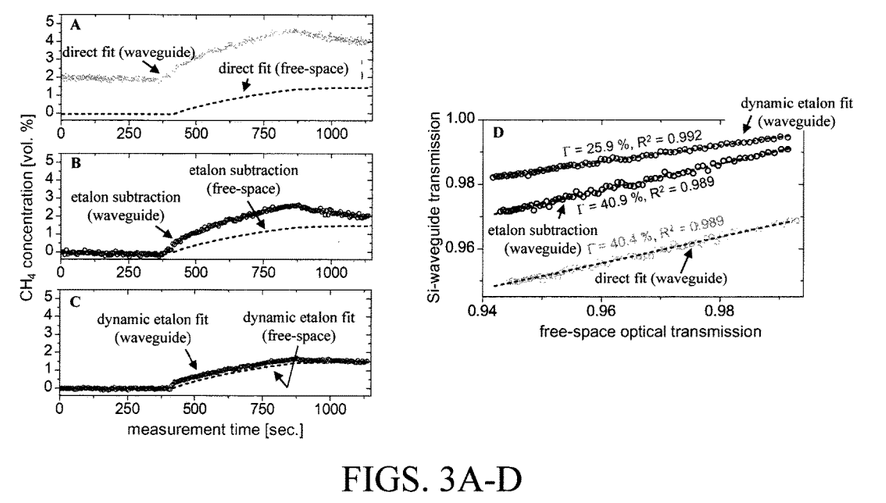
FIG. 3A is a diagram illustrating direct fitting of the raw waveguide sensor data in FIG. 2A using a Voigt profile, in comparison to the same applied to data acquired using a conventional free-space reference sensor, according to an embodiment of the present invention.

FIGS. 3A-D illustrate a comparison of DEF-R (FIG. 3C) to conventional techniques, in terms of tracking the $CH_4$ concentration extracted from the reference free-space sensor: (i) direct fitting using a Voigt profile (convolution of homogenous Lorentzian and inhomogenous Gaussian profiles) (FIG. 3A), and (ii) conventional etalon subtraction (FIG. 3B). The dashed line in each case corresponds to the free-space spectrometer measurement (utilizing 10 centimeter (cm) path length, in contrast to the ~2.6 cm optical path length of the silicon-photonic (SiPh) waveguide sensor. As shown in FIG. 3C, only the DEF-R process yields agreement with the free-space sensor reference. Furthermore, the free-space system noise-equivalent absorption (NEA) is ~40× better than the SiPh chip, and is an adequate concentration reference.

Clear accuracy benefit of DEF-R is demonstrated in comparison to both direct Voigt fitting and conventional subtraction. In the case of direct Voigt fitting (FIG. 3A), initial accuracy deviation is caused by absorption-like etalons, which produce a measurement offset. In the conventional subtraction example (FIG. 3B) initial accuracy is correct via zero-gas subtraction, but etalon drifts over time yield poor accuracy for longer measurement intervals. In contrast to the first two techniques, DEF-R (FIG. 3C) is capable of removing the initial offset and maintaining long-term accuracy ($>10^3$ s). Furthermore, the correlation between the free-space sensor and SiPh chip sensor is plotted in FIG. 3D, yielding reasonable optical confinement factors only in the case where DEF-R is employed (25.9%, in good agreement with COMSOL mode-profile simulations). In FIG. 3D, the slope of the line is an experimental measure of the effective overlap factor $\Gamma$ of the waveguide optical mode with the surrounding ambient air.

Figure 4A:
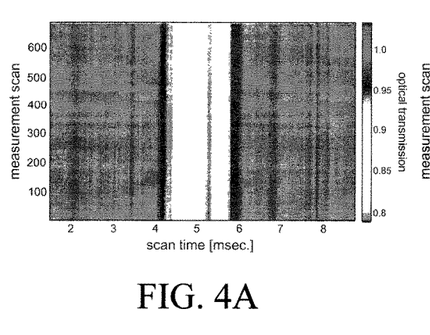
FIG. 4A is a diagram illustrating raw spectral compilation of 700 sequential traces, captured during optical transmission through a 10% CH4 reference cell, located inline with a silicon waveguide chip sensor exhibiting transmission etalons.
Figure 4B:
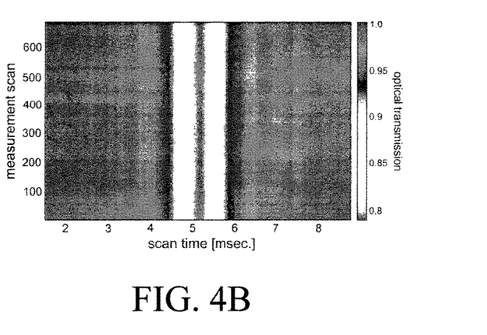
FIG. 4B is a diagram illustrating the same data as in FIG. 4A, but analyzed with DEF-R showing the visible enhancement of $CH_4$ spectral absorption in the presence of high gas concentrations, according to an embodiment of the present invention.

The utility of DEF-R for large dynamic range (i.e., analyte high-concentration limit) was also demonstrated. See FIGS. 4A and 4B which show the utilization of DEF-R on a high-concentration in-line reference gas sample. Specifically, FIGS. 4A and 4B show the use of DEF-R in the case of a 10% $CH_4$ reference cell in-line with a silicon waveguide chip sensor. In this case the clear removal of etalons in the wing is apparent, resulting in excellent spectral retrieval visibility over >600 measurement scans. Thus, DEF-R is effective at high analyte gas concentrations in addition to the aforementioned prior demonstration of DEF-R for analyte absorption below fringe amplitude levels. The concentration retrieval in this case yields white noise performance over the duration of the measurement, whereas direct Voigt fitting does not provide the same $Hz^{-1/2}$ performance at longer time-scales.

Figure 5A:
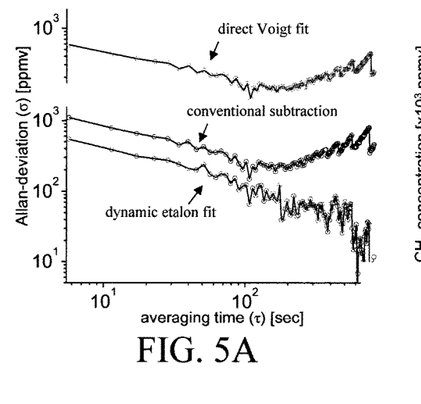
FIG. 5A is a diagram illustrating Allan-deviation curves for a zero-gas line-scanning over 2000 seconds using DEF-R as compared to direct Voigt fit and conventional subtraction according to an embodiment of the present invention.
Figure 5B:
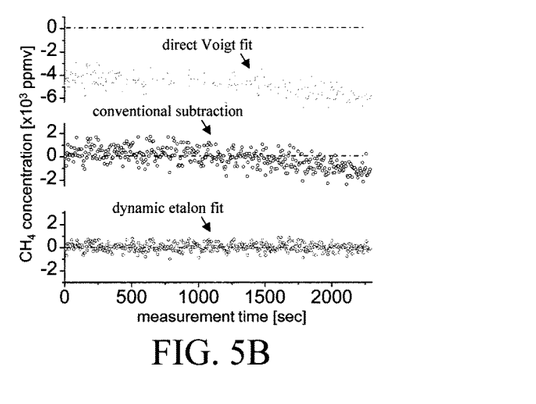
FIG. 5B is a diagram illustrating the retrieved concentrations for the samples in FIG. 5A according to an embodiment of the present invention.

Allan-deviation Analysis of DEF-R Stability Enhancement: The DEF-R technique is empirically justified in the context of FIGS. 2-4, where a clear accuracy enhancement is observed for a large dynamic range. To characterize rigorously the benefits of DEF-R, zero-gas line-scanning over 2000 seconds was used, and the retrieved concentrations are plotted in FIG. 5B along with the associated Allan-deviation curves in FIG. 5A. As shown in FIG. 5B, in the case of a direct Voigt fit, a large initial concentration offset is observed (which is expected since concentration retrieval artifacts are introduced by etalon-like absorption features), followed by a concentration drift over time (corresponding to the etalon drifts). Conventional subtraction is capable of removing the initial offset, but the static nature of the subtraction prevents any correction to the long-term fringe drifts causing a false concentration deviation (i.e. measurement inaccuracy). Advantageously, DEF-R eliminates both the initial imprecision (visible in the tighter points which indicate enhanced short-term precision) and long-term inaccuracies. The associated Allan-deviation is plotted adjacent to the time-series, demonstrating Gaussian-noise performance up to $10^3$ seconds, and a short-term precision improvement by ~2×. See FIG. 5A.

Figure 6:
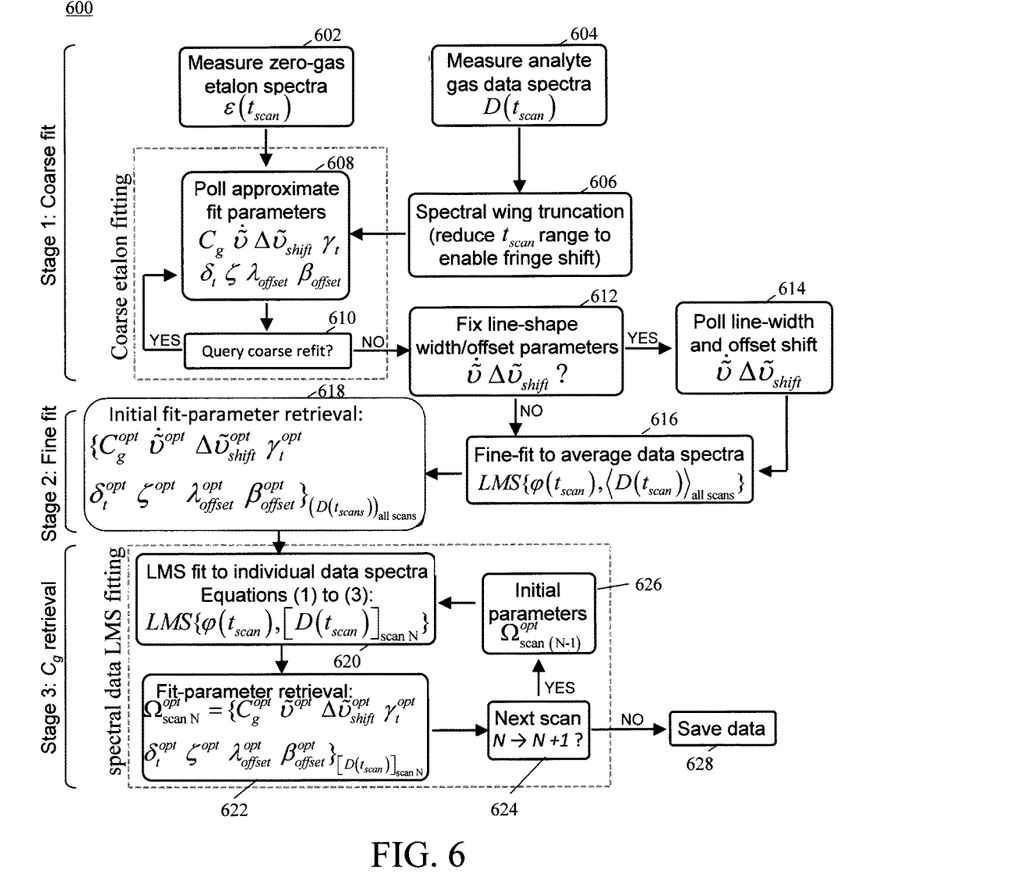
FIG. 6 is a diagram illustrating an exemplary methodology for dynamic etalon fitting for adaptive background noise reduction in etalon-noise dominated optical sensors according to an embodiment of the present invention.

Given the above, an exemplary methodology 600 for dynamic etalon fitting for adaptive background noise reduction in an etalon-noise dominated optical sensor is now described by way of reference to FIG. 6. As will be described in detail below, the fitting routine performed in methodology 600 is subdivided into three main stages: (1) a coarse fitting to average data spectra via user input; (2) fine-least-mean square (LMS) fitting using coarse-fit parameters; and (3) spectral data fitting with continuous parameter updates for enhanced LMS efficiency. The steps performed in each of these stages are now described in detail.

Stage 1: Coarse Fit—To begin the process, data is acquired in step 602 from a zero-gas etalon spectrum $\varepsilon(t_{scan})$ and in step 604 from an analyte gas data spectrum $D(t_{scan})$ both measured using the optical sensor. Both spectra are sampled identically with M total sample points.

In step 606, the spectral wings of the data spectrum $D(t_{scan})$ are truncated by $M_{trunc}$ points on both the start and end of the spectrum. The length of $D(t_{scan})$ is reduced to $(M-2 \cdot M_{trunc})$ points, allowing freedom of horizontal shift without extending beyond the original time window occupied by the original raw zero-gas etalon trace.

In step 608, a user is asked (i.e., polling the user) to provide approximate fit parameter values, if available. It is assumed herein that the user is someone well-acquainted with the sensor and sensor data. For example, these approximate fit parameter values may be available from prior sensor calibration/functional tests, performed by fitting a sequence of raw zero-gas traces over operationally relevant set environmental/ambient parameters, where the fit parameters are saved and then retrieved in step 608 from a lookup table. Alternatively the user can provide such fit parameters manually (i.e., at the time of request), or by any other means of interfacing with the algorithm. A transformed zero-gas trace $\Gamma[\varepsilon(t_{scan})]$ can then be generated using the approximate fit parameters and the zero-gas etalon spectrum $\varepsilon(t_{scan})$ data (acquired in step 602).

In step 610, a heuristic determination is made as to whether the coarse fit performed in step 608 is acceptable (or not). Based on prior knowledge of sensor fringe free-spectral range and fractional amplitude variation, the satisfactoriness of the coarse fit is qualified by the maximum allowable deviation such that LMS convergence is attainable. According to an exemplary embodiment, step 610 is carried out heuristically (i.e., based on user determination or maximum allowable deviation computed from an internal look-up table—for instance in the absence of the user, an initial guess for the fit can be determined by a simple look-up table based on the fringe structure (i.e., periodicity and amplitude) which will have maximum error tolerance vs. fringe amplitude/period) comparing $\Gamma[\varepsilon(t_{scan})]$ and $\varphi(t_{scan})$. If it is determined in step 610 that (Yes) a refit is needed, then steps 608 and 610 are repeated with updated parameters. The idea here is that within some error bound, the initial parameters are acceptable if LMS convergence can be achieved. Empirically, this condition is not difficult to attain because the spectral fringe structure is complex and there is generally only a 'unique' way to shift the zero gas 'correctly' to minimize the residuals.

On the other hand, if it is determined in step 610 that (No) further refitting is not needed, then in step 612 a determination is made as to whether (or not) to fix the lineshape parameters. As provided above, the lineshape parameters can include scan-time to wavenumber conversion $\tilde{\upsilon}$ and line-center shift $\Delta\tilde{\upsilon}_{shift}$. Generally, $\tilde{\upsilon}$ indicates the width of the line, and $\Delta\tilde{\upsilon}_{shift}$ locates the center of the line. Accordingly, these lineshape parameters may also be referred to herein as "line-shape width/offset parameters"). The lineshape width/offset parameters can be fixed using a high-concentration gas reference. By way of example only, fixed (i.e., not variable) lineshape parameters may be preferable in the weak-signal regime where signal absorption amplitude is less than the fringe amplitude.

If it is determined in step 612 that (Yes) fixed lineshape parameters should be used, then in step 614 the user is polled for the lineshape parameters (i.e., the user inputs lineshape parameters which are retrieved in step 614). Again, the user can provide such parameters manually (i.e., at the time of request), or by any other means of interfacing with the algorithm. On the other hand, if it is determined in step 612 that (No) it is not necessary to fix the fixed lineshape parameters, then variable lineshape parameters will be used in the process (see below). Methodology 600 then proceeds into the fine fitting (second) stage.

It is notable that the coarse fit performed, e.g., in steps 608 and 610 is in some cases optional and may be omitted if the measured zero-gas etalon spectra are similar (i.e., the free-spectral range and fractional intensity variation difference is below the maximum allowable deviation for fit convergence) to the analyte data spectra. Namely, the purpose of steps 608/610 is to determine an initial set of fitting parameters, and this may not be necessary if the zero-gas trace in step 602 is well represented in step 604. For instance, steps 608/610 are not needed in the case where the zero-gas trace serves as a good starting point (i.e., no transformation is required). In this case the starting fit parameters are those that give a unity transformation (this is equivalent to not transforming $\varepsilon(t_{scan})$ and using it directly). Running stage 2 of the DEF-R process will then take care of the small perturbations that the zero-gas trace actually experiences during a long-term measurement. However, in cases where variation may be significant due to environmental factors, the above-described coarse alignment process will ensure convergence of the least-mean square (LMS) fitting algorithm (see below).

Stage 2: Fine Fit—As provided above, user-provided (fixed) lineshape parameters may be obtained in step 614. Alternatively, fine-fit can be performed directly to total average data spectrum $<D(t_{scan})>_{all\ scans}$ via least-mean squared (LMS) fitting. In either case, this fine-fitting is performed in step 616. As highlighted above, if the option in step 614 is selected, then the lineshape parameters are fixed and not varied during the LMS procedure. The remaining initial fit parameters are those determined during step 608 (see above), or in the case of stable fringe structure, the zero-gas trace may be used directly (i.e., unity fit-parameter transformation of the zero-gas trace, such that $\Gamma[\varepsilon(t_{scan})]=\varepsilon(t_{scan})$.

The fit parameters are refined to best match to the features of $<D(t_{scan})>_{all\ scans}$. According to an exemplary embodiment, fit iterations are stopped using a set of convergence parameters appropriate for minimizing fit error, fitting time, and maximizing fit algorithm stability across the widest range of operating/environmental conditions possible. In step 618, the fit parameters are retrieved, and used (in the third stage) as the initial fit parameters for time-sequence of spectral scans. As provided above, these fit parameters determined using the present process extend the usefulness of the zero-gas scan (from step 602) by accounting for etalon drift.

Stage 3: Analyte Concentration Retrieval—In step 620, LMS fitting is used for each spectral acquisition $[D(t_{scan})]_{scan}\ N$ in sequential order of data acquired. Fit-parameters, denoted by the variable set $\Omega_{scan\ N}^{opt}$, are retrieved in step 622.

In step 624, a determination is made as to whether there is additional scan data. If it is determined in step 624 that (Yes) there is additional scan data to process, then the iterative LMS fit procedure is continued on subsequent spectral acquisitions. Namely, in step 626 the initial parameters are updated for sequential LMS fit to previous optimum $\Omega_{scan\ N}^{opt}$. This allows significant reduction in fit time and improved algorithm convergence efficiency by providing near-optimum initial parameters (assuming fringe drifts in the adiabatic limit). The update in step 626 can occur as part of some temporary memory buffer wherein, for example, the starting fit parameters for each trace is updated as part of a 'for loop'.

On the other hand, if the end of sequential data spectra is reached and a determination is made in step 624 that (No) there is no additional scan data to process, then the data is saved in step 628 and the process completes.

Implementations of the DEF-R algorithm involve the selective use of free-parameters to maximize fringe reduction. The free-parameters, along with their associated transformations as described by Equations 1-3 (see above), are as follows:

(i) $C_g$— analyte concentration. This parameter introduces a wavelength specific absorption based on the Voigt lineshape profile.

(ii) $\tilde{\upsilon}$—scan-time to wavenumber conversion. This indicates the width of the line and can be fixed in the limit of small concentrations where the etalon effects dominate.

(iii) $\Delta\tilde{\upsilon}_{shift}$—wavenumber offset shift. The offset shift locates the center of the line. Similar to (ii), this parameter is measured and can be fixed using a high-concentration gas reference.

(iv) $\gamma_t$—horizontal stretch. Introduction of uniformly stretched etalon effects, based primarily on laser ringing during the ramp transition phase which induces a nonlinear time-to-frequency conversion on the x-axis scale.

(v) $\delta_t$—etalon shift. Shifts of the etalon are caused by changes in free-spectral range (FSR) based on external environmental effects (e.g. thermal variations).

(vi) $\zeta$—vertical stretch. Polarization effects cause relative intensity variations of the fringe amplitudes. These small polarization perturbations may be accounted for by using this term.

(vii) $(\lambda_{offset}\cdot t_{scan})+\beta_{offset}$—slope offset. A first-order linear slope term that corrects any normalization inaccuracy due to power drifts in the spectral wings (where linear baseline normalization is employed).

The above free-parameters (of which a subset or the entire parameter space may be used for fitting concurrently) cover to first order all significant sources of drift for etalon-dominated systems. Experimental results also demonstrate that in the case of low fringe amplitudes (i.e., fringe noise does not dominate the signal-to-noise ratio), the DEF-R algorithm does not adversely affect the sensitivity, which is to be expected and demonstrates that DEF-R can be generally used in most systems without deteriorating the sensor performance.

An alternative embodiment of DEF-R involves the removal of not only optical fringes but also fixed high-concentration in-line reference gas cell absorption. The present process would proceed in the same manner as described above, but merely requires the presence of a well-sealed reference gas cell such that the fractional absorption remains constant. Such an in-line cell has utility in wavelength referencing for line-locking and concentration calibration, although this signal (being measured in series with the target analyte) will dominate the measured analyte. The DEF-R algorithm may be employed to remove this background reference spectrum, and is particularly useful in the case of a simulated reference gas (of a difference type than the sample analyte, but possessing a center transition near the analyte to be measured). In such a case, the lineshape profiles of reference and sample are dissimilar, which allows selective removal and background fitting of such interferences in addition to unwanted etalons.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network: The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 7:
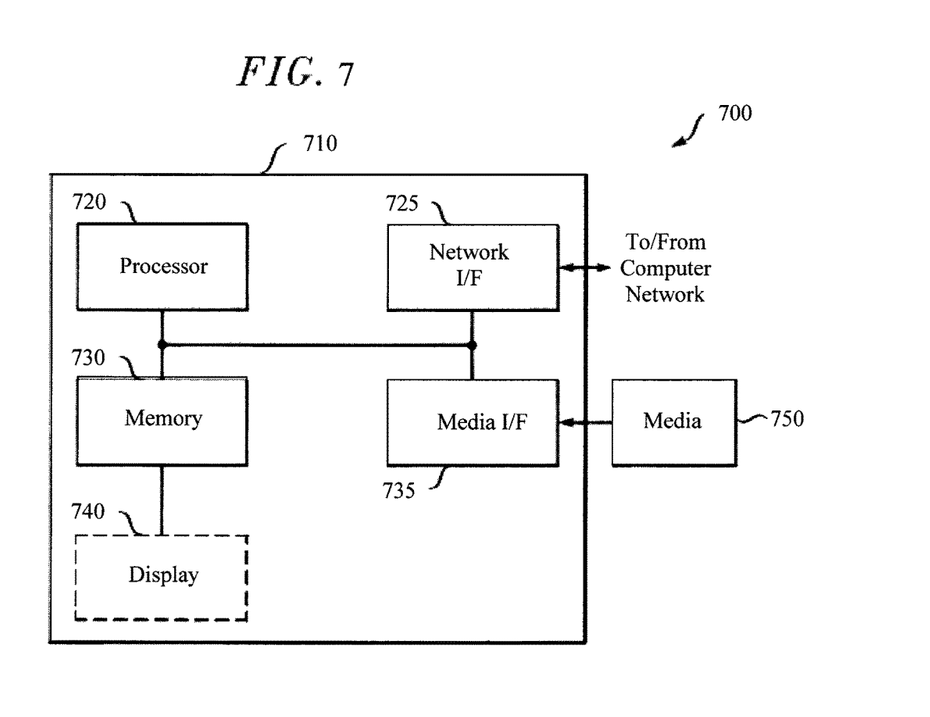
FIG. 7 is a diagram illustrating an exemplary apparatus for performing one or more of the methodologies presented herein according to an embodiment of the present invention.

Turning now to FIG. 7, a block diagram is shown of an apparatus 700 for implementing one or more of the methodologies presented herein. By way of example only, apparatus 700 can be configured to implement one or more of the steps of methodology 600 of FIG. 6.

Apparatus 700 includes a computer system 710 and removable media 750. Computer system 710 includes a processor device 720, a network interface 725, a memory 730, a media interface 735 and an optional display 740. Network interface 725 allows computer system 710 to connect to a network, while media interface 735 allows computer system 710 to interact with media, such as a hard drive or removable media 750.

Processor device 720 can be configured to implement the methods, steps, and functions disclosed herein. The memory 730 could be distributed or local and the processor device 720 could be distributed or singular. The memory 730 could be implemented as an electrical, magnetic or optical memory, or any combination of these or other types of storage devices. Moreover, the term "memory" should be construed broadly enough to encompass any information able to be read from, or written to, an address in the addressable space accessed by processor device 720. With this definition, information on a network, accessible through network interface 725, is still within memory 730 because the processor device 720 can retrieve the information from the network. It should be noted that each distributed processor that makes up processor device 720 generally contains its own addressable memory space. It should also be noted that some or all of computer system 710 can be incorporated into an application-specific or general-use integrated circuit.

Optional display 740 is any type of display suitable for interacting with a human user of apparatus 700. Generally, display 740 is a computer monitor or other similar display.

In conclusion, the present dynamic etalon fitting-routine (DEF-R) enables precision and accuracy enhancement in trace-gas concentration retrieval. Systems dominated by fringe drifts will benefit most from this technique, with spectral cleanup, accuracy enhancement, and stability improvement being the most significantly observed benefits. Empirically, there is negligible crosstalk between fit parameters, resulting in substantially enhanced sensor performance for trace-gas applications, and enabling performance far beyond fringe-dominated noise-equivalent absorptions.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method for a dynamic etalon fitting routine (DEF-R) for adaptive background noise reduction in an optical sensor, the method comprising steps of:
   obtaining a zero-gas spectrum measured using the optical sensor, wherein the optical sensor comprises a silicon-photonic waveguide chip sensor;
   obtaining an analyte gas spectrum of a target trace gas measured using the optical sensor and a free-space reference spectrometer enclosed within a sealed environmental chamber as a reference;
   comparing the zero-gas spectrum and the analyte gas spectrum using fit parameters that compensate for drifting etalons in the optical sensor; and
   dynamically extracting the drifting etalons from the analyte gas spectrum to retrieve concentration of the target trace gas,
   wherein the method further comprises the steps of:
   obtaining approximate fit parameters from a user;
   generating a transformed zero-gas spectrum using the zero-gas spectrum and the approximate fit parameters; and
   calculating a dynamic spectrum given as a product of the analyte gas spectrum and the transformed zero-gas spectrum.

2. The method of claim 1, wherein the zero-gas spectrum and the analyte gas spectrum both comprise M total sample points.

3. The method of claim 2, further comprising a step of:
   truncating the analyte gas spectrum by $M_{trunc}$ points on both a start and an end of the analyte gas spectrum.

4. The method of claim 1, further comprising a step of:
   obtaining the approximate fit parameters from a look up table in which user input is stored.

5. The method of claim 1, further comprising a step of:
   requesting the user manually provide the approximate fit parameters.

6. The method of claim 1, further comprising a step of:
   applying the fit parameters to a time-sequence of individual spectral scans.

7. The method of claim 6, further comprising the steps of:
   applying an initial set of fit parameters to each of the individual spectral scans; and
   retrieving the fit parameters for each of the individual spectral scans.

8. The method of claim 7, further comprising a step of:
   updating the initial set of fit parameters for each of the individual spectral scans.

9. The method of claim 1, wherein the drifting etalons comprise a free-spectral range shift due to thermal variations in the optical sensor.

10. The method of claim 9, wherein the drifting etalons comprise second order fringe variations due to the free-spectral range shift.

11. The method of claim 1, wherein the drifting etalons comprise variations in absorption amplitude.

12. The method of claim 1, wherein the drifting etalons comprises anomalies in power normalization.

13. A non-transitory computer program product for DEF-R for adaptive background noise reduction in an optical sensor, the computer program product comprising a computer readable storage medium having program instructions embodied therewith, the program instructions executable by a computer to cause the computer to:
   obtain a zero-gas spectrum measured using the optical sensor, wherein the optical sensor comprises a silicon-photonic waveguide chip sensor;
   obtain an analyte gas spectrum of a target trace gas measured using the optical sensor and a free-space reference spectrometer enclosed within a sealed environmental chamber as a reference;
   compare the zero-gas spectrum and the analyte gas spectrum using fit parameters that compensate for drifting etalons in the optical sensor; and
   dynamically extract the drifting etalons from the analyte gas spectrum to retrieve concentration of the target trace gas,
   wherein the program instructions further cause the computer to:
   obtain approximate fit parameters from a user;

generate a transformed zero-gas spectrum using the zero-gas spectrum and the approximate fit parameters; and calculate a dynamic spectrum given as a product of the analyte gas spectrum and the transformed zero-gas spectrum.

14. The non-transitory computer program product of claim 13, wherein the zero-gas spectrum and the analyte gas spectrum both comprise M total sample points, and wherein the program instructions further cause the computer to:

truncate the analyte gas spectrum by $M_{trunc}$ points on both a start and an end of the analyte gas spectrum.

15. The non-transitory computer program product of claim 13, wherein the program instructions further cause the computer to:

apply the fit parameters to a time-sequence of individual spectral scans.

16. The non-transitory computer program product of claim 15, wherein the program instructions further cause the computer to:

apply an initial set of fit parameters to each of the individual spectral scans; and retrieve the fit parameters for each of the individual spectral scans.

17. The non-transitory computer program product of claim 16, wherein the program instructions further cause the computer to:

update the initial set of fit parameters for each of the individual spectral scans.

\* \* \* \* \*